US012077829B2

(12) United States Patent
Eloit et al.

(10) Patent No.: US 12,077,829 B2
(45) Date of Patent: *Sep. 3, 2024

(54) ANELLOVIRUS GENOME QUANTIFICATION AS A BIOMARKER OF IMMUNE SUPPRESSION

(71) Applicants: INSTITUT PASTEUR, Paris (FR); UNIVERSITÉ PARIS CITÉ, Paris (FR); ASSISTANCE PUBLIQUE—HOPITAUX DE PARIS, Paris (FR); PATHOQUEST, Paris (FR); ECOLE NATIONALE VETERINAIRE D'ALFORT, Maison Alfort (FR)

(72) Inventors: Marc Eloit, Paris (FR); Justine Cheval, Paris (FR); Charles Hebert, Houilles (FR); Marc Lecuit, Paris (FR)

(73) Assignees: INSTITUT PASTEUR, Paris (FR); UNIVERSITÉ PARIS CITÉ, Paris (FR); ASSISTANCE PUBLIQUE—HOPITAUX DE PARIS, Paris (FR); PATHOQUEST, Paris (FR); ECOLE NATIONALE VETERINAIRE D'ALFORT, Maison Alfort (FR)

( * ) Notice: Subject to any disclaimer, the term of this patent is extended or adjusted under 35 U.S.C. 154(b) by 203 days.

This patent is subject to a terminal disclaimer.

(21) Appl. No.: 16/205,659

(22) Filed: Nov. 30, 2018

(65) Prior Publication Data

US 2019/0085418 A1  Mar. 21, 2019

Related U.S. Application Data

(63) Continuation of application No. 14/395,105, filed as application No. PCT/EP2013/058231 on Apr. 19, 2013, now Pat. No. 10,144,975.

(30) Foreign Application Priority Data

Apr. 20, 2012 (EP) .................................... 12305462

(51) Int. Cl.
  *C12Q 1/68* (2018.01)
  *C12Q 1/70* (2006.01)

(52) U.S. Cl.
  CPC ....... *C12Q 1/701* (2013.01); *C12Q 2600/106* (2013.01); *C12Q 2600/158* (2013.01)

(58) Field of Classification Search
  None
  See application file for complete search history.

(56) References Cited

U.S. PATENT DOCUMENTS

2011/0045019 A1  2/2011 Meng

FOREIGN PATENT DOCUMENTS

WO  2010/008480 A2  1/2010

OTHER PUBLICATIONS

Gravitt et al; Journal of Virological methods, vol. 112, pp. 23-33, 2003.*
Communication Pursuant to Rule 114(2) EPC and attached Third Party Observations With Respect to EP 13 717 292.0-1404, Publication No. EP 2 839 040 A1, Apr. 28, 2017.
Philippe Biagini, et al., "Comparison of systems performance for TT virus detection using PCR primer sets located in non-coding and coding regions of the viral genome," Journal of Clinical Virology, vol. 22, pp. 91-99 (2001).
Masashi Ninomiya, et al., "Development of PCT Assays with Nested Primers Specific for Differential Detection of Three Human Anelloviruses and Early Acquisition of Dual or Triple Infection during Infancy, Journal of Clinical Microbiology," vol. 46, No. 2, pp. 507-514 (2008).
H. Okamoto, "History of Discoveries and Pathogenicity of TT Viruses, Current Topics in Microbial Immunology," vol. 331, pp. 1-20 (2009).
Blast search result of a 16 nucleotide oligo (AGCGAAGTCAAGGGGC) of Seq ID No. 4, cited in Third Party Observations With Respect to EP 13 717 292.0-1404, Publication No. EP 2 839 040 A1, Apr. 28, 2017.
Blast search result of a 16 nucleotide oligo (GAATGGCAGAGTTTCA) of Seq ID No. 5, cited in Third Party Observations With Respect to EP 13 717 292.0-1404, Publication No. EP 2 839 040 A1, Apr. 28, 2017.
Thom and Petrik, Journal of Medical Virology, vol. 79, pp. 1-7, 2007.
Fishman, Infection in Solid-Organ Transplant Recipients N Engl. J Med 2007;357:2601-2614.
Fishman, Infections in immunocompromised hosts and organ transplant recipients: essentials. Liver Transpl. Nov. 2011;17 Suppl 3:S34-7.
Hutchinson P, Laboratory assessment of immune function in renal transplant patients. Nephrol Dial Transplant. May 2003;18(5):983-9.
Moen, Effect of immune modulation on TT virus (TTV) and TIN-like-mini-virus (TLMV) viremia. J Med Virol. May 2003;70(1):177-82.

(Continued)

*Primary Examiner* — Jehanne S Sitton
(74) *Attorney, Agent, or Firm* — Arrigo, Lee, Guttman & Mouta-Bellum LLP

(57) ABSTRACT

The present invention relates to the use of the measure of anelloviral load for the determination of immunosuppression. More precisely, the present invention provides a method for characterizing the immunosuppressed or non-immunosuppressed status of a subject, comprising the steps of determining the anelloviral load from a biological sample of the said subject, and determining from the said comparison the immunosuppressed or non-immunosuppressed status. The determination of the immunosuppressed status of the subject can then be used to design or adapt a therapeutic treatment.

18 Claims, No Drawings

Specification includes a Sequence Listing.

(56) References Cited

OTHER PUBLICATIONS

Moen, Serum concentrations of TT virus and TT virus-like mini virus in patients developing AIDS. AIDS. Aug. 16, 2002;16(12):1679-82.
Christensen, Prevalence and prognostic significance of infection with TT virus in patients infected with human immunodeficiency virus. J Infect Dis. May 2000;181(5):1796-9. Epub May 15, 2000.
Shibayama, Inverse relationship between the titre of TT virus DNA and the CD4 cell count in patients infected with HIV. AIDS. Mar. 30, 2001;15(5):563-70.
Touinssi, TT virus infection: prevalence of elevated viraemia and arguments for the immune control of viral load. J Clin Virol. May 2001;21(2):135-41.
Moen, Real-time PCR methods for independent quantitation of ITV and TLMV. J Virol Methods. Jun. 2002;104(1):59-67.
Biagini P, Circular genomes related to anelloviruses identified in human and animal samples by using a combined rolling-circle amplification/sequence-independent single primer amplification approach. J Gen Virol, Oct. 2007;88(Pt 10):2696-701.
Hino Si, Miyata H. Torque teno virus (ITV): current status. Rev Med Virol. Jan.-Feb. 2007; 17(1):45-57.
Leary T, Improved detection systems for TT virus reveal high prevalence in humans, non-human primates and farm animals. J Gen Virot. Aug. 1999;80 (Pt 8):2115-20.
Bentley DR Accurate whole human genome sequencing using reversible terminator chemistry. Nature. Nov. 6, 2008;456(7218):53-9. doi:10.1038/nature07517.
Margulies M Genome sequencing in microfabricated high-density picolitre reactors. Nature. Sep. 15, 2005;437(7057):376-80. Epub Jul. 31, 2005.
McKernan Sequence and structural variation in a human genome uncovered by short-read, massively parallel ligation sequencing using two-base encoding. Genome Res. Sep. 2009;19(9):1527-41. oi:10.1101/gr.091868.109. Epub Jun. 22, 2009.
Harris TD, Single-molecule DNA sequencing of a viral genome. Science. Apr. 4, 2008;320(5872):106-9. doi: 10.1126/science.1150427.
Eid, Real-time DNA sequencing from single potymerase molecules. Science. Jan. 2, 2009;323(5910):133-8. doi: 10.1126/science.1162986. Epub Nov. 20, 2008.
Rothberg JM, An integrated semiconductor device enabling non-optical genome sequencing. Nature. Jul. 20, 2011;475(7356):348-52. doi: 10.1038/nature10242.
Ctarke J, Continuous base identification for single-molecule nanopore DNA sequencing. Nat Nanotechnot. Apr. 2009;4(4):265-70. doi: 10.1038/nnano.2009.12. Epub Feb. 22, 2009.
Smith TF, Overlapping genes and information theory. J Theor Blot. Jul. 21, 1981;91(2):379-80.
Needleman, Wunsch, A general method applicable to the search for similarities in the amino acid sequence of two proteins. J Mot Blot 48(3): 443-453, 1970.
Pearson WR, Lipman DJ. Improved tools for biological sequence comparison. Proc Natl Acad Sci U S A. Apr. 1988;85(8):2444-8.
Vogetstein B, Kinzter KW. Digital PCR. Proc Natt Acad Sci U S A. Aug. 3, 1999;96(16):9236-41.
Madsen, ITV viral load as a marker for immune reconstitution after initiation of HAART in HIV-infected patients. HIV Clin Trials. Jul.-Aug. 2002;3(4):287-95.
Maggi F, Torque teno virus viremia load size in patients with selected congenital defects of innate immunity. Ctin Vaccine Imrnunot. Apr. 2011;18(4):692-4. doI: 10.1128/CVI.00466-10. Epub Feb. 16, 2011.
Jelcic, Isolation of Multiple TT Virus Genotypes from Spleen Biopsy Tissue from a Hodgkin's Disease Patient: Genome Reorganization and Diversity in the Hypervariable Region, J Virot. Jul. 2004; 78(14): 7498-7507. doi: 10.1128/N1.78.14.7498-7507.2004.
De Villiers, The Diversity of Torque Teno Viruses: In Vitro Replication Leads to the Formation of Additional Replication-Competent Subvirat Molecules J Virot. Jul. 2011; 85(14): 7284-7295.
Okamoto, Marked Genomic Heterogeneity and Frequent Mixed Infection of TT Virus Demonstrated by PCR with Primers from Coding and Noncoding Regions. Virology, 259, 2, 428-436, 1999.
Maggi, TT Virus Loads and Lymphocyte Subpopulations in Children with Acute Respiratory Diseases, J Virot. Aug. 2003; 77(16): 9081-9083.

\* cited by examiner

SEQUENCE LISTING

<160> NUMBER OF SEQ ID NOS: 7

<210> SEQ ID NO 1
<211> LENGTH: 3853
<212> TYPE: DNA
<213> ORGANISM: Torque teno virus

<400> SEQUENCE: 1

```
attttgctac gtcactaacc acgtgacacc cacaggccaa ccgaatgcta tgtcatccat        60
ttcctgggcc gggtctacgt cctcatataa gtaagtgcac ttccgaatgg ctgagttttc       120
cacgcccgtc cgcagcggtg aagccacgga gggagatctc cgcgtcccga gggcgggtgc       180
cgaaggtgag tttacacacc gaagtcaagg ggcaattcgg gctcgggact ggccgggcta       240
tgggcaaggc tctgaaaaaa gcatgtttat tggcaggcat tacagaaaga aaagggcgct       300
gtcactgtgt gctgtgcgaa caacaaagaa ggcttgcaaa ctactaatag taatgtggac       360
cccacctcgc aatgatcaac actaccttaa ctggcaatgg tactcaagta tacttagctc       420
ccacgctgct atgtgcgggt gtcccgacgc tgtcgctcat tttaatcatc ttgcttctgt       480
gcttcgtgcc ccgcaaaacc cacccccctcc cggtccccag cgaaacctgc ccctccgacg       540
gctgccggct ctcccggctg cgccagaggc gcccggagat agagcaccat ggcctatggc       600
tggtggcgcc gaaggagaag acggtggcgc aggtggagac gcagaccatg gaggcgccgc       660
tggaggaccc gaagacgcag acctgctaga cgccgtggcc gccgcagaaa cgtaaggaga       720
cgccgcagag gagggaggtg gaggaggaga tataggagat ggaaagaaa gggcaggcgc       780 agaaaaaaag ctaaataat aataagacaa tggcaaccaa actacagaag gagatgtaac       840
atagtaggct acatccctgt actaatatgt ggcgaaaata ctgtcagcag aaactatgcc       900
acacactcag acgataccaa ctacccagga ccctttgggg ggggtatgac tacagacaaa       960
tttactttaa gaattctgta tgacgagtac aaaaggttta tgaactactg gacagcatct      1020
aacgaagacc tagacctttg tagatatcta ggagtaaacc tgtacttttt cagacaccca      1080
gatgtagatt ttatcataaa aattaatacc atgcctcctt ttctagacac agaactcaca      1140
gcccctagca tacacccagg catgctagcc ctagacaaaa gagcaagatg gatacctagc      1200
ttaaaatcta gaccgggaaa aaaacactat attaaaataa gagtaggggc accaagaatg      1260
ttcactgata aatggtaccc ccaaacagat ctttgtgaca tggtgcttct aactgtctat      1320
gcaaccgcag cggatatgca atatccgttc ggctcaccac taactgactc tgtggttgtg      1380
aacttccagg ttctgcaatc catgtatgat aaaacaatta gcatattacc agacgaaaaa      1440
tcacaaagag aaattctact taacaagata gcaagttaca ttcccttta taataccaca      1500 caaactatag cccaattaaa gccatttata gatgcaggca atgtaacatc aggcgcaaca      1560
gcaacaacat gggcatcata cataaacaca accaaatta ctacagcaac cacaacaact      1620
tatgcatatc caggcaccaa cagaccccca gtaactatgt taacctgtaa tgactcctgg      1680
tacagaggaa cagtatataa cacacaaatt caacagttac caataaaagc agctaaatta      1740
tacttagagg caacaaaaac cttgctagga aacaccttca caaatgagga ctacacacta      1800
gaatatcatg gaggactgta cagctcaata tggctatccc ctggtagatc ttactttgaa      1860
acaacaggag catatacaga cataaagtac aatccatca cagacagagg agaaggcaac      1920
atgttatgga tagactggct aagcaaaaaa aacatgaact atgacaaagt acaaagtaaa      1980
tgcttaatat cagacctacc tctatgggca gcagcatatg gatatgtaga attttgtgca      2040
aaaagtacag gagaccaaaa catacacatg aatgccaggc tactaataag aagtcccttt      2100
```

```
acagacccac aactactagt acacacagac cccacaaaag gctttgttcc ttactcttta    2160
aactttggaa atggtaaaat gccaggaggt agtagtaatg tgcctattag aatgagagct    2220
aaatggtatc caacattatt tcaccagcaa gaagtactag aggccttagc acagtcaggc    2280
cccttttgcat accactcaga cattaaaaaa gtatctctgg gtatgaaata ccgttttaag    2340
tggatctggg gtggaaaccc cgttcgccaa caggttgtta gaaatccctg caagaaacc     2400
cactcctcgg gcaatagagt ccctagaagc ttacaaatcg ttgacccgaa atacaactca    2460
ccggaactca cattccatac ctgggacttc agacgtggcc tctttggccc gaaagctatt    2520
cagagaatgc aacaacaacc aacaactact gacattttt cagcaggccg caagagaccc     2580
aggagggaca ccgaggtgta ccactccagc caagaagggg agcaaaaaga aagcttactt    2640
ttccccccag tcaagctcct cagacgagtc ccccgtggg aagactcgca gcaggaggaa     2700
agcgggtcgc aaagctcaga ggaagagacg cagaccgtct cccagcagct caagcagcag    2760
ctgcagcaac agcgaatcct gggagtcaaa ctcagactcc tgttcaacca agtccaaaaa    2820
atccaacaaa atcaagatat caaccctacc ttgttaccaa gggggggga tctagcatcc     2880
ttatttcaaa tagcaccata acatgtttg gtgaccccaa accttacaac ccttccagta     2940
atgactggaa agaggagtac gaggcctgta gaatatggga cagaccccc agaggcaacc     3000
taagagatac ccctttctac ccctgggccc caaggaaaaa ccagtaccgt gtaaacttta    3060
aacttggatt ccaataaagc taggccgtgg gactttcact tgtcggtgtc tgcttataaa    3120
agtaactaag cactccgagc gaagcgagga gtgcgaccct tggggctca acgccttcgg    3180
agccgcgcgc tacgccttcg gctgcgcgcg gcacctcaga ccccgctcg tgctgacacg     3240
ctcgcgcgtg tcagaccact tcgggctcgc ggggtcggg aaatttacta aacagactcc     3300
gagttgccat tggactcagg agctatgaat cagtaacgaa agtgagtggg gccagacttc    3360
gccataaggc ctttatcttc ttgccatttg tcagtaacag gggtcgccat agacttcggc    3420
ctccactttta ccttgtaaaa actaccaaaa tggccgttcc agtgacgtca cagccgccat    3480
tttaagtagc tgacgtcaag gattgacgta aaggttaaag gtcatcctcg gcggaagcta    3540
cacaaaatgg tggacaacat cttccgggtc aaaggttgtg cgtacgtcac aagtcacgtg    3600
gagggacccc gctgtaaccc ggaagtaggc cccgtcacgt gacttaccac gtgtgtacac    3660
gtcaccgccg ccatttttgtt ttacaaaatg gctgacttcc ttcctctttt ttgaaaaaag    3720
gcgccaaaaa accgtcggcg ggggggccgc gcgctgcgcg cgcggccccc gggggaggc    3780
attgcctccc ccccccgcgc gcatgcgcgc gggtccccc ccctccgggg ggctccgccc    3840
cccggccccc ccc                                                       3853
```

<210> SEQ ID NO 2
<211> LENGTH: 3242
<212> TYPE: DNA
<213> ORGANISM: Torque teno midi virus 1

<400> SEQUENCE: 2

```
aggtggagac tcttaagcta tataaccaag tggggtggcg aatggctgag tttaccccgc      60
tagacggtgc agggaccgga tcgagcgcag cgaggaggtc cccggctgcc cgtgggcggg     120
agcccgaggt gagtgaaacc accgaggtct aggggcaatt cgggctaggg cagtctagcg     180
gaacgggcaa gaaacttaaa aatatttctt ttacagatgc aaaacctatc agccaaagac     240
ttctacaaac catgcagata caactgtgaa actaaaaacc aaatgtggat gtctggcatt     300
```

```
gctgactccc atgacagttg gtgtgactgt gatactcctt ttgctcacct cctggctagt      360
attttcctc  ctggtcacac agatcgcaca cgaaccatcc aagaaatact taccagagat      420
tttaggaaaa catgccttc  tggtggggcc gacgcaacaa attctggtat ggccgaaact      480
atagaagaaa aagagaaga  tttccaaaaa gaagaaaaag aagatttac  agaagaacaa      540
aatatagaag acctgctcgc cgccgtcgca gacgcagaag gaaggtaaga agaaaaaaaa      600
aaactcttat agtaagacaa tggcagccag actctattgt actctgtaaa attaaagggt      660
atgactctat aatatgggga gctgaaggca cacagtttca atgttctaca catgaaatgt      720
atgaatatac aagacaaaag taccctgggg gaggaggatt tggtgtacaa ctttacagct      780
tagagtattt gtatgaccaa tggaaactta gaaataatat atggactaaa acaaatcaac      840
tcaaagattt gtgtagatac ttaaaatgtg ttatgacctt ttacagacac caacacatag      900
attttgtaat tgtatatgaa agacaacccc catttgaaat agataaacta acatacatga      960
aatatcatcc atatatgtta ttacaaagaa agcataaaat aattttacct agtcaaacaa     1020
ctaatcctag aggtaaatta aaaaaaaaga aaactattaa acctcccaaa caaatgctca     1080
gcaaatggtt ttttcaacaa caatttgcta aatatgatct actacttatt gctgcagcag     1140
catgtagttt aagataccct agaataggct gctgcaatga aaatagaatg ataaccttat     1200
actgtttaaa tactaaattt tatcaagata cagaatgggg aactacaaaa caggcccccc     1260
actactttaa accatatgca acaattaata aatccatgat atttgtctct aactatggag     1320
gtaaaaaaac agaatataac ataggccaat ggatagaaac agatatacct ggagaaggta     1380
atctagcaag atactacaga tcaataagta agaaggagg  ttacttttca cctaaaatac     1440
tgcaagcata tcaaacaaaa gtaaagtctg tagactacaa acctttacca attgttttag     1500
gtagatataa cccagcaata gatgatggaa aaggcaacaa aatttactta caaactataa     1560
tgaatggcca ttggggccta cctcaaaaaa caccagatta tataatagaa gaggtccctc     1620
tttggctagg cttctgggga tactataact acttaaaaca aacaagaact gaagctatat     1680
ttccactaca catgtttgta gtgcaaagca aatacattca aacacaacaa acagaaacac     1740
ctaacaattt tgggcatttt atagacaaca gcttttataca gggcaaaaac ccatgggact     1800
cagttattac ttactcagaa caaaagctat ggtttcctac agttgcatgg caactaaaaa     1860
ccataaatgc tatttgtgaa agtggaccat atgtacctaa actagacaat caaacatata     1920
gtacctggga actagcaact cattactcat ttcactttaa atggggtggt ccacagatat     1980
cagaccaacc agttgaagac ccaggaaaca aaaacaaata tgatgtgccc gatacaatca     2040
aagaagcatt acaaattgtt aacccagcaa aaaacattgc tgccacgatg ttccatgact     2100
gggactacag acggggttgc attacatcaa cagctattaa aagaatgcaa caaaacctcc     2160
caactgattc atctctcgaa tctgattcag actcagaacc agcacccaag aaaaaaagac     2220
tactaccagt cctccacgac ccacaaaaga aacggaaaa  gatcaaccaa tgtctcctct     2280
ctctctgcga agaaagtaca tgccaggagc aggaaacgga ggaaacatc  ctcaagctca     2340
tccagcagca gcagcagcag cagcagaaac tcaagcacaa cctcttagta ctaatcaagg     2400
acttaaaagt gaaacaaaga ttattacaac tacaaacggg ggtactagaa taacccttac     2460
cagatttaaa ccaggatttg agcaagaaac tgaaaaagag ttagcacaag catttaacag     2520
accccctaga ctgttcaaag aagataaacc cttttacccc tggctaccca gatttacacc     2580
ccttgtaaac tttcacctta attttaaagg ctaggcctac actgctcact tagtggtgta     2640
tgtttattaa agtttgcacc ccagaaaaat tgtaaaataa aaaaaaaaaa aaaaaataaa     2700
```

-continued

```
aaattgcaaa aattcggcgc tcgcgcgcgc tgcgcgcgcg agcgccgtca cgcgccggcg      2760
ctcgcgcgcc gcgcgtatgt gctaacacac cacgcaccta gattggggtg cgcgcgtagc      2820
gcgcgcaccc caatgcgccc cgccctcgtt ccgacccgct tgcgcgggtc ggaccacttc      2880
gggctcgggg gggcgcgcct gcggcgctta tttactaaac agactccgag tcgccattgg      2940 gccccccccta agctccgccc ccctcatgaa tattcataaa ggaaaccaca aaattagaat     3000
tgccgaccac aaactgccat atgctaatta gttccccttt tacacagtaa aaaggggaag     3060 tggggggggca gagccccccc acaccccccg cgggggggc agagccccccc ccgcaccccc    3120 cctacgtcac aggccacgcc cccgccgcca tcttgggtgc ggcagggcgg ggactaaaat     3180
ggcgggaccc aatcatttta tactttcact ttccaattaa aacccgccac gtcacacaaa     3240
ag                                                                    3242
```

<210> SEQ ID NO 3
<211> LENGTH: 2915
<212> TYPE: DNA
<213> ORGANISM: Torque teno mini virus 9
<220> FEATURE:
<221> NAME/KEY: misc_feature
<222> LOCATION: (2865)..(2866)
<223> OTHER INFORMATION: n is a, c, g, or t
<220> FEATURE:
<221> NAME/KEY: misc_feature
<222> LOCATION: (2875)..(2876)
<223> OTHER INFORMATION: n is a, c, g, or t
<220> FEATURE:
<221> NAME/KEY: misc_feature
<222> LOCATION: (2893)..(2894)
<223> OTHER INFORMATION: n is a, c, g, or t

<400> SEQUENCE: 3

```
taataaatat tcataaagga aaccgctaat ttgaattgcc gaccacaaac tgacatatgc       60
aaattaactt ctgcaattta ccttaacttc ctcaaaaatt aattaataat catcgtcaca      120
gtgggaggag actctacact atataatcaa ctacacttcc gaatggctga gtttatgccg      180
ccagacggag actggagcag ttcactgatt acaggctgac caaggcgggg tgccgaaggt      240
gagtgaaacc accgaagtca aggggcaatt cgggctaggt cagtctggcg gaacgggcaa      300
gaaacttaaa ataattttat tttacagaat gtcaagatat attccaacaa atcaacact       360 tagacaaaaa aaactacaat ggatgaatct aattgtgcac ggccacgaca tcttttgtga     420
ctgctgcaaa ccacttgaat gcaccattgg aaccataatt aaccaagaac caaacctaaa     480
atttaacaca gaagaaaaaa atctacttaa aaaatgcctt tctacaaaag atggagacgc     540
tggcgctggc gccgcagacc ccgacggctt tggagaagga gatttagacg ccctctttac     600
agaagatttt ggagaagaaa atacaggta  agaaaaagaa aacttaaata cttacccta     660 agacaatggc aacctcatta tattaacaaa ctaaaagtac aaggatggta cccactagca     720
atatcaacta agacagact  atcaaataac ttaaacttat atttagaaag cattgcgccg     780
cattatttac atggtggggg aggatttaca atatgtaact tttctttaat gactttatat     840
caagaaaacc ttgtatgtag aaactggtgg acaaaaggaa atgaaaatat gcctttaatt     900
agatacctag gatgtgaaat taccttatat agacaagctg aagtagacta catggtatat     960
gtacataatt cttatcctat gtcagctaat ttattaacat atcaaagtac atgcccacaa     1020
gttatgctta tgaacaatag aacaaaaata atgccttgta aaagatataa tagaaacaaa     1080
aaaccttaca aaaaattctt tgtaaaacca ccttctcaat tacaaaacaa atggtacttt     1140
```

-continued

```
caaaaggaac tatctaacgt tccacttatg caagttatgg ctacaacttg ctcgttagac      1200
cgcatgtacc tttcctcatc atcagtttca accacaatgg gttttgtaag cttagatact      1260
aacggtttca tggaaagata tatgaaagac aatggaacag caccatactc cccattaaca      1320
ggacaaataa ttttgctgc accaaacggt gacaatgtaa taacaaatat accctagga       1380 caatgcatat tattaggaac agtaacagac tatacaccag gaacccaact ttcatccata      1440
accttaaata cgggtgcact cagtcccct tcagattggg gaacctttaa gtcagcatct      1500
aaagcaattt ataatgcata ctatcaacac aaatattggg gaaatccatt ttttacaaac      1560
tggttccatg gtgaccaaag aatgatagct acaggcaaaa ccttaaaaga actttgtcaa      1620
atatacaaag atgacgatat aaccacagct aaactaaaag aaggctttat atttaaagaa      1680
caaaagtggg tagaactcag atacaaccca tgggcagata aggaaaagg taatatggta       1740 tatttattac ccattaatga acatcaacac tcttatggct gggcaccacc aacaaacaaa      1800
gatataataa cacaagatct accctcaac atattactgt ggggatacct agattttcac       1860
agaaaagcaa aacatacaa tgacatagac acaacatgtc tactagtcat aaaatctcct       1920
tacctatatc caaaggaca aattactttt gctgttcctt tagatcaaga atttctagat       1980
ggtaactcac catactttac tgaaggtcac aaaacacaat cagaccaaca atattggcat      2040 ccaaagtaa gatttcaaac tagaaccgtt aatgccatag catgtacagg cccaggaaca      2100 acaaattac caccagatgt tagtactgaa tttcatatga aatataaatt tcgttttaag       2160
attggaggag aaccagcacc catgtctgta ctcaaaaacc cagatgaaca accaacctat      2220
accatcccca ataacctcct acaaacaact tcgttgcaga gtccaacaac accatttgaa      2280
tacctcctct ggaactttga cgaacgcaga ggagagctta caaaaagagc tgcaaaaga       2340 attactcaaa acatccaaac tgaaacaaat gttttgccaa ttacagagtc agcagcctgg      2400
tgtccagcaa cacaccgaaa acacaagac ccatcggaga catcgacctc ggaagaagac       2460
gaaacactca cgacggagga gaaactactc cagcagcgaa gagagcaaaa actcctccac      2520
aaactcatca gacgacagtt actcagacta accacatcag aataaagaca ttaaatgttt      2580
ctatgtttgc agatactccc actccaaata ggagaatgac tacctgggaa tatgagcaag      2640
agttagagga tgctaaaata tggtgtagag tacctagaac atatatacat gatcacccaa      2700
cctatccctg gtcccagaa gtacctaaat atactgtaaa cttgactta aacgcgccgc       2760 aataaactca aggcctgcaa aatttcactc tcggtgtcca tttatataag tttaaacctt      2820
aataaacatc caccacactc ccaaatacgc aggcgcagag ggggnnccgc ccccnnagac      2880 ccccagggg ggnnaagccc cccctcaaac ccccc                                  2915
```

```
<210> SEQ ID NO 4
<211> LENGTH: 36
<212> TYPE: DNA
<213> ORGANISM: artificial
<220> FEATURE:
<223> OTHER INFORMATION: primer

<400> SEQUENCE: 4
ascgvagtca aggggcmwwt cgggcdsgsk sggtra                                 36

<210> SEQ ID NO 5
<211> LENGTH: 33
<212> TYPE: DNA
<213> ORGANISM: artificial
<220> FEATURE:
<223> OTHER INFORMATION: primer
```

```
<400> SEQUENCE: 5
gaatggywga gtttywcbhc gccsgtysgy rga                                33

<210> SEQ ID NO 6
<211> LENGTH: 15
<212> TYPE: DNA
<213> ORGANISM: artificial
<220> FEATURE:
<223> OTHER INFORMATION: primer

<400> SEQUENCE: 6
cgaatggctg agttt                                                    15

<210> SEQ ID NO 7
<211> LENGTH: 12
<212> TYPE: DNA
<213> ORGANISM: artificial
<220> FEATURE:
<223> OTHER INFORMATION: primer

<400> SEQUENCE: 7
gggcgggtgc cg                                                       12
```

ANELLOVIRUS GENOME QUANTIFICATION AS A BIOMARKER OF IMMUNE SUPPRESSION

The present invention relates to the use of the measure of anelloviral load for the determination of immunosuppression. More specifically, the invention relates to a method for the diagnosis of immunosuppression in a subject based on anellovirus viral load.

The immune system defends an organism against aggressions such as pathogen infection, cellular transformation, and physical or chemical damage. When the immune system is less active than normal, immunodeficiency or immunosuppression occurs, resulting in life-threatening infections or cancer. Immunosuppression is a condition in which the immune system's ability to fight diseases, for example infectious diseases or cancer, is compromised or entirely absent. Immunosuppression takes various forms, and may affect either the innate or the adaptive immune system, or both, depending of the source of the deficiency. It usually results in recurring or life-threatening infections.

Immunosuppression can either be the result of diseases, or be produced by pharmaceuticals or an infection, resulting in an increased susceptibility to secondary infections by pathogens such as bacteria and viruses.

Many diseases are thus characterized by the development of progressive immunosuppression in the patient. The presence of an impaired immune response in patients with malignancies (e.g. leukemia, lymphoma, multiple myeloma) is well documented. Progressive immunosuppression has also been observed in certain chronic infection such as AIDS, sepsis, leprosy, cytomegalovirus infections, malaria, lupus, and the like. Immunodeficiency is also a potential adverse effect of many therapeutic treatments (radiotherapy or chemotherapy for example). In such a situation of non-deliberate immunosuppression, patients are usually treated with immunostimulants (e.g. cytokines), in order to boost the patient's immune system. However, immunostimulants lack specificity, in that they activate the immune system in general. If not administered cautiously, they may trigger an overactivation of the immune system, resulting in poor tolerance Alternatively, immunosuppression may result from deliberate intent to weaken the immune system. In general, deliberately induced immunosuppression is performed by administration of immunosuppressive drugs, in order to prevent the body from rejecting an organ transplant or for the treatment of auto-immune diseases. Immunosuppressive treatments, however, when inappropriate or inadequate, may lead to an over-immunosuppression state where the patient is extremely vulnerable to infections. Indeed, opportunistic infections and malignancies remain a significant cause of death after transplantation and are obvious consequences of over-immunosuppression.

Because of the great diversity of causes, and because each of those causes may affect the immune system in a different aspect, different diagnosis for immunosuppression have been developed. Some nonspecific and pathogen-specific measures of cell-mediated immune function are available (Fishman et al. N Engl J Med. 2007, Fishman et al. Liver Transpl. 2011). Cell mediated immune function assays include lymphocyte subset analysis, particularly $CD4^+$ T cell numbering or measure of the CD4+/CD8+ T cell ratio, neutrophil function assay, NK activation assay, lymphocyte proliferation assay (Hutchinson et al. Nephrol Dial Transplant 2003).

Those assays however are not sufficiently sensitive to detect slight changes in the immune system. Additionally, each of those assays focus on assaying the integrity of a specific pathway or mechanism of the immune system. None of them is based on assaying the end result, which is the capability of the immune system to respond to or control infections.

Currently there is a no universal method for the diagnosis of immunosuppression that could be used universally, that is, for any suspected cause of immunosuppression. There is thus a ongoing need for a rapid, reliable and non-invasive test assessing precisely the immune status of a patient. Especially, a diagnosis method that would allow for evaluation of the capacity of the immune system to respond to infections could be used to fine-tune immunosuppressive treatments to the proper needs of the patients, and avoid over-immunosuppression.

The inventors have found that the anelloviral load is a reliable marker of immune status and can thus be used for the diagnosis of immunosuppression.

DETAILED DESCRIPTION

Anelloviruses (ANV) are viruses that infect more than 90% individuals. Mixed infections with several strains and ANV species are frequent, and most subjects host at least one of them, but no pathological consequence has been attributed to ANV infection. In particular, no clear correlation between the anelloviral load and the immune state of the subject has been identified in the prior art. Patients on immunosuppressive treatment generally showed an increase in the load of specific viral strains (e.g. TLMV and TTV). However, the inter-individual variations were such that the only relevant information could be obtained from examining the changes in the viral load of each individual. In particular, no conclusion could be drawn from the comparison of groups of patients, treated or not treated. Thus the methods of the prior art did not enable the determination of the immunosuppressive status of a subject and the design of a specific treatment thereof (Moen et al., *J Med Virol,* 70(1): 177-182, 2003; Moen et al., *AIDS,* 16(12): 1679-1682, 2002; Christensen et al., *J Infect Dis,* 181: 1796-1799, 2000; Shibayama et al., *AIDS,* 15: 563-570, 2001; Touinssi et al., *J Clin Virol,* 21: 135-141, 2001).

In contrast, the present inventors have surprisingly found that the anelloviral load can be used as a marker for immunosuppression. Whereas previous studies were based on PCR, and thus were highly dependent upon primers design, resulting in missing variants of this highly variable virus (Moen et al., *J Virol Methods,* 104(1): 59-67, 2002), the present inventors used High Throughput Sequencing (HTS). This technique led to the identification of a broad and unbiased range of ANV sequences, enabling the present inventors to demonstrate the existence of a correlation between the anelloviral load and immunosuppression with a high degree of confidence. In particular, the inventors have found that immunosuppressed subjects have a higher anelloviral load by comparison with healthy subjects.

The measure of the global load of the viruses from the family of anelloviruses can thus be used as a marker of the immune state of the subject. More precisely, according to the invention, a high anelloviral load in a subject indicates that the said subject is immunosuppressed.

Thus, in a first aspect, the invention relates to a method for characterizing the immunosuppressed or non-immunosuppressed status of a subject, comprising the steps of:

a) determining the anelloviral load from a biological sample of the said subject, and
b) assessing from the determination of step a) the immunosuppressed or non-immunosuppressed status.

The term "immunosuppression" (or "immunodepression" or "immunodeficiency"), as used herein, refers to the reduction or suppression of the immune system function, i.e. immunosuppression generally denotes a state when a subject's specific and/or non-specific immune system function is reduced or absent. The whole immune response may be depressed, or a particular population of immunologically active lymphocytes may be selectively affected. In some cases, the effect may be preferentially on T cells rather than B cells. If B cells are affected, it may be on a specific subclass of antibody-producing cells. Antigen-specific immunosuppression may be the result of deletion or suppression of a particular clone of antigen-specific cells, or the result of enhanced regulation of the immune response by antigen-specific suppressor cells. It can also be the result of increased production of antiidiotypic antibody.

Immunosuppression may result from certain diseases such as AIDS or lymphoma or from certain drugs such as some of those used to treat cancer. Immunosuppression may also be deliberately induced with drugs, as in preparation for bone marrow or other organ transplantation to prevent the rejection of the transplant. Thus immunosuppression according to the invention may be from any origin such as, for example, but not limited to, immunosuppressive treatment, immunosuppressive side effects of drugs or therapy including radiotherapy, inherited immunosuppressive genetic traits or diseases, acquired immunosuppressive diseases such as AIDs, cancers such as leukemia or lymphoma.

By "immunosuppressed status" it is herein referred to a condition where the immune system function of a subject is reduced or absent. Thus, according to the invention the terms "immunosuppressed", "immunodepressed" or "immunocompromised" are all deemed to carry the same meaning. In a particular embodiment, the "immunosuppressed status" of the subject means the ability of the subject to control viral infection, that is to say, the ability of the subject to prevent viral amplification from said viral infection.

It is difficult to precisely asses the immunosuppressed status of a subject with the methods of the prior art. This may lead to situations where too high a dose of an immunosuppressive treatment is given to a patient in need thereof. It is also possible that a dose not high enough of an immunostimulating treatment is administered to a patient, because the immunosuppressed status of the said patient was not correctly determined. The consequences for the patient's health are potentially serious in either situation. For example, immunosuppressive treatments, when inappropriate or inadequate, may lead to an over-immunosuppression state, which leaves the patient highly susceptible to infections. On the other hand, it is important to be capable of identifying reliably chronically immunosuppressed patients, so as to provide them with the most adequate treatment.

The method of the invention allows the precise determination of the immunosuppressed status of the subject, enabling a specific treatment to be tailored to the needs of the patient. The prior determination of the immunosuppressed status of the patient with the method of the invention thus lead to a treatment safer than the treatments designed on the basis of the methods of the prior art.

Thus the present invention also relates to a method for designing an immunomodulation treatment for a subject, said method comprising:

a) determining from a biological sample of a subject the anelloviral load, and
b) assessing from the determination of step a) the immunosuppressed or non-immunosuppressed status, and
c) designing the immunomodulation treatment according to said immunosuppressed or non-immunosuppressed status assessed in step b)

The invention is also drawn to a method of treatment of a condition associated with immunodeficiency. As used herein; "conditions associated with immunodeficiency" or "immunodeficiency disorders" refer to a diverse group of conditions characterized primarily by an increased susceptibility to various opportunistic infections with consequent severe acute, recurrent or chronic disease. In a first embodiment, this increased susceptibility to infection results from immunosuppression due to one or more defects in the immune system. Immunosuppression in this case is non-deliberate. Immunodeficiency disorders encompass, without limitation, "immunodeficiency syndromes" wherein all features are the result of the immune defect, and "syndromes with immunodeficiency", wherein some, even prominent features cannot be explained by the immune defect. By means of example and not limitation, diseases and conditions associated with immunodeficiency or immunosuppression comprise: human immunodeficiency virus (HIV) infection and acquired immune deficiency syndrome (AIDS), hypogammaglobulinemia, hematologic cancers such as leukaemia and lymphoma, lymphocytopenia (lymphopenia) of any origin, lupus erythematosus, cachexia, opioids abuse, mastocytosis, rheumatic fever, trypanosomiasis, alcohol abuse.

The group of immunodeficiency disorders also encompasses diseases and conditions associated with immunosuppression arising from an artificial, usually controlled diminution or prevention of a subject's immune response. Immunosuppression in subjects is thus deliberately induced. It may be caused by immunosuppressive treatment, or it may occur as a side effect of a therapy of other indications (e.g., side effect of cancer chemotherapy). These latter conditions include such conditions as total bone marrow ablation, bone marrow transplantation, organ transplantation, treatment with immunosuppressive drugs such as inter alia tacrolimus, cyclosporine, methotrexate, mycophenolate, azathioprine, interferons, and immunoglobulins such anti-CD20 and anti-CD3; and treatments with: chemotherapy agents, corticosteroids, anti-TNF drugs, radiation.

Thus the present invention also relates to a method for treating a condition associated with immunodeficiency in a subject, said method comprising:
a) determining the immunosuppressed or non-immunosuppressed status of the said subject according to the methods of the invention, and
b) adapting an immunomodulation treatment to the said subject.

The present invention thus provides an immunomodulation treatment for use in treating a condition associated with immunodeficiency in a subject, wherein the use comprises the steps of:
a) the immunosuppressed or non-immunosuppressed status of the said subject is determined according to the methods of the invention, and
b) the said immunomodulation treatment is adapted to the said subject.

In other words, the invention relates to the use of an immunomodulation treatment in the preparation of a medicament for treating a condition associated with immunodeficiency in a subject, wherein:

a) the immunosuppressed or non-immunosuppressed status of the said subject is determined according to the methods of the invention, and b) the said immunomodulation treatment is adapted to the said subject.

By "immunomodulation treatment", it is herein referred to any treatment intended to induce, enhance, inhibit or suppress an immune function. According to a preferred embodiment, an immunomodulation treatment is an immunosuppressive treatment. According to another preferred embodiment, an immunomodulation treatment is an immunostimulating treatment.

By "immunosuppressive treatment" it is herein referred to any treatment intended to inhibit or suppress an immune function of a subject that would be adverse to a desired clinical outcome. Immunosuppressive treatments include for example treatments that are intended to induce immune function deficiency in a subject in order to treat the said subject with a transplant of cells or of an organ. They also include for example treatments that induce immune function deficiency as a side effect, such as chemotherapy or radiotherapy. Immunosuppressive treatments usually include e.g. glucocorticoids, antiproliferative and antimetabolic drugs (rapamycin, everolimus, mycophenolate mofetil, mycophenolic acid), calcineurin inhibitors (cyclosporine, FK506, voclosporin), S1P-R agonists (FTY720), malononitrilamides (FK778), and antibodies (e.g. antithymocyte globulin) including monoclonal antibodies (e.g. muromonab-CD3, daclizumab, basiliximab, rituximab, alemtuzumab, infliximab, adalimumab, efalizumab).

An "immunostimulating treatment", according to the present invention, is any type of treatment intended to induce or enhance immune function. Immunostimulating treatments include treatments that stimulate specific immune response, treatments that stimulate non-specific immune response and treatments that stimulate both specific and non-specific immune responses. Such immunostimulating treatments are usually given to treat conditions associated with non-deliberate immunosuppression. Immunostimulating treatments that stimulate the immune response have been described in the literature, ranging from small synthetic molecules (poly I:C, levamisole, inosine pranobex) to living microorganisms (*Corynebacterium parvum*), and including complex mixtures of bacterial components with mineral oils (Freund's adjuvant) or inorganic salts (aluminum and magnesium hydroxide/phosphate) and, more recently, recombinant proteins modulating immunity (e.g. cytokines, antibodies against cellular receptors). According to the present invention anti-viral treatments are also considered immunostimulating treatments. Anti-viral treatments include for example oseltamivir (Tamiflu), zanamivir (Relenza), interferon, which inhibit viral synthesis in infected cells, particularly alpha-interferon, used in the treatment of hepatitis B and C.

Thus, in one embodiment of the method of the invention, the immunomodulation treatment is an immunosuppressive treatment. In another embodiment of the method of the invention, the immunomodulation treatment is an immunostimulating treatment.

The said adaptation of the immunomodulation treatment may be either a reduction or suppression of the said immunomodulation treatment or the continuation of the said immunomodulation treatment at the same or an increased dose. The skilled person will appreciate that the treatment will be continued if the desired effect on the subject's immune system is not achieved. For example, when the treatment is administered for stimulating the immune system function in order to compensate for a deficit thereof, the treatment is continued if the patient shows an immunosuppressed phenotype. Likewise, an immunosuppressive treatment will be continued if the subject displays a non-immunosuppressed status. On the other hand, the treatment will be reduced or suppressed if the desired effect on the subject's immune system has been attained. This is the case for example when the treatment seeks to obtain immunosuppression in order to perform e.g. organ transplantation, while the subject shows an immunosuppression status.

In a preferred embodiment, the condition associated with immunodeficiency is transplant rejection.

Thus, the invention relates to a method for treating or preventing transplant rejection in a transplanted subject, said method comprising:

a) determining the immunosuppressed or non-immunosuppressed status of the said transplanted subject according to the methods of the invention, and b) adapting an immunosuppressive treatment to the said transplanted subject.

The present invention thus provides an immunosuppressive treatment for use in treating or preventing transplant rejection in a transplanted subject, wherein the said use comprises the steps of:

a) determining the immunosuppressed or non-immunosuppressed status of the said transplanted subject according to the methods of the invention, and b) adapting the said immunosuppressive treatment to the said transplanted subject.

In other words, the invention relates to the use of an immunosuppressive treatment in the preparation of a medicament for treating or preventing transplant rejection in a transplanted subject, wherein:

a) the immunosuppressed or non-immunosuppressed status of the transplanted said subject is determined according to the methods of the invention, and b) the said immunosuppressive treatment is adapted to the said transplanted subject.

In another preferred embodiment, the condition associated with immunodeficiency is an infection.

Thus this embodiment relates to a method of treating an infection in an infected subject, said method comprising:

a) determining the immunosuppressed or non-immunosuppressed status of the said infected subject according to the methods of the invention, and b) adapting an immunostimulating treatment to the said infected subject.

The present invention thus provides an immunostimulating treatment for use in treating an infection in an infected subject, wherein the use comprises the steps of:

a) determining the immunosuppressed or non-immunosuppressed status of the said transplanted subject according to the methods of the invention, and b) adapting the said immunostimulating treatment to the said subject.

In other words, the invention relates to the use of an immunostimulating treatment in the preparation of a medicament for treating an infection in an infected subject, wherein:

a) the immunosuppressed or non-immunosuppressed status of the transplanted said subject is determined according to the methods of the invention, and b) the said immunostimulating treatment is adapted to the said transplanted subject.

An anellovirus according to the invention is a non-enveloped virus, with a small circular single-stranded DNA genome which is replicated through double-stranded intermediates, and which may contain up to 4 open reading frames: ORF1, ORF2, ORF3 and ORF4. Open reading frames (ORF) 1 (long) and 2 (short) are partially overlapping. ORF3 and ORF4 are smaller. Anelloviruses are subgrouped into torque teno virus (TTV), torque teno mini virus (TTMV), and torque teno midi virus (TTMDV), with known hosts including humans, non-human primates and domestic animals (Biagini et al., *J Gen Virol*, 88: 2696-2701, 2007; Hino Et Miyata, *Rev Med Virol*, 17: 45-57, 2007; Leary et al., *J Gen Virol*, 80: 2115-2120, 1999).

By "anellovirus", it is herein referred to any virus belonging to the Anelloviridae family of viruses, including, but not limited to, the Torque Teno viruses (TTVs), the Torque Teno midiviruses (TTMDVs), and the Torque Teno miniviruses, also formerly known as the Torque Teno-like miniviruses (TTMVs). The prototype strain of Torque Teno Virus (TTV-1a) has a genome size of 3853 nucleotides. The prototype strain of Torque Teno Minivirus, formerly known as TTV-like minivirus (TTMV-NLC030), has a genome size of 2915 nucleotides. Finally, the Torque Teno Midivirus has been described, with a genome of 3242 nucleotides for the prototype strain (TTMDV-MD1-073). Anelloviruses are highly variable in sequence. For example, nucleotide sequences of full-length genomes of TTV can vary by 40%, and those of TTMDV by 33%.

The "viral load" according to the invention is the number of nucleic acid sequences of a virus present in a biological sample. The viral load reflects the severity of a viral infection. Preferably, the viral load refers to the proportion of a nucleic acid sequences in a biological sample which belong to the said virus. More preferably, the viral load represents the number of copies of the said virus in a biological sample.

The viral load can for example be determined by estimating the amount of the virus in a biological sample from a subject.

As used herein, the term "subject" refers to a vertebrate, preferably a mammal, and most preferably a human.

By "biological sample", it is herein referred to any sample that is taken from a subject, which includes but is not limited to, for example, blood, serum, plasma, sputum, urine, stool, skin, cerebrospinal fluid, saliva, gastric secretions, semen, seminal fluid, tears, spinal tissue or fluid, cerebral fluid, trigeminal ganglion sample, a sacral ganglion sample, adipose tissue, lymphoid tissue, placental tissue, upper reproductive tract tissue, gastrointestinal tract tissue, male genital tissue and fetal central nervous system tissue. Preferably, the biological sample is blood or is derived from blood, such as plasma or serum.

According to the invention, the anelloviral load in a subject means the viral load of any virus of the Anelloviridae family hosted by said subject. Thus determining the anelloviral load in a subject according to the invention comprises estimating the number of sequences of any virus of the Anelloviridae family in a biological sample from the said subject. In particular, there is no selection, according to the invention, of specific anellovirus species to be measured in the said biological sample. Preferably, determining the anelloviral load comprises determining the amount of active and/or inactive viral copies. It comprises determining the amount of circulating, integrated or latent viral copies. More preferably, the anelloviral load corresponds to circulating copies of anellovirus.

The levels of anellovirus may be determined by measuring levels of anellovirus DNA, anellovirus RNA, or anellovirus proteins. The method according to the invention may thus comprise another preliminary step, between the taking of the sample from the patient and step a) as defined above, corresponding to the transformation of the biological sample into a double-stranded DNA (dsDNA) sample, or into an mRNA (or corresponding cDNA) sample, or into a protein sample, which is then ready to use for in vitro detection of anellovirus in step a). The said dsDNA may correspond either to the whole anellovirus genome or only to a portion of it. Once a ready-to-use dsDNA, mRNA (or corresponding cDNA) or protein sample is available, the detection of the anellovirus may be performed, depending on the type of transformation and the available ready-to-use sample, either at the genomic DNA (i.e. based on the presence of at least one sequence consisting of at least a part of the anellovirus genome), mRNA (i.e. based on the mRNA content of the sample) or at the protein level (i.e. based on the protein content of the sample).

Preferably, the levels of anellovirus are determined by measuring levels of anellovirus DNA.

Methods for detecting a nucleic acid in a biological sample include inter alia hybridization with a labelled probe, amplification, including PCR amplification, sequencing, and all other methods known to the person of skills in the art. The amount of nucleic acid transcripts can be measured by any technology known by the skilled person. In particular, the measure may be carried out directly on an extracted messenger RNA (mRNA) sample, or on retrotranscribed complementary DNA (cDNA) prepared from extracted mRNA by technologies well-known in the art. From the mRNA or cDNA sample, the amount of nucleic acid transcripts may be measured using any technology known by a person skilled in the art, including nucleic microarrays, quantitative PCR, and hybridization with a labelled probe.

In a first embodiment of the invention, the levels of anellovirus DNA are measured by sequencing. As used herein, the term "sequencing" is used in a broad sense and refers to any technique known by the skilled person including but not limited to Sanger dideoxy termination sequencing, whole-genome sequencing, sequencing by hybridization, pyrosequencing, capillary electrophoresis, cycle sequencing, single-base extension sequencing, solid-phase sequencing, high-throughput sequencing, massively parallel signature sequencing (MPSS), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD® sequencing, MS-PET sequencing, mass spectrometry, and combinations thereof.

Optionally, DNA is fragmented randomly, generally by physical methods, prior to sequencing. The anellovirus DNA may be sequenced by any technique known in the art, including sequencing by ligation, pyrosequencing, sequencing-by-synthesis or single-molecule sequencing. Sequencing also includes PCR-based techniques, such as for example quantitative PCR or emulsion PCR.

Sequencing is performed on the entire DNA contained in the biological sample, or on portions of the DNA contained in the biological sample. It will be immediately clear to the skilled person that the said sample contains at least a mixture of anellovirus DNA and of DNA from the host subject. Moreover, the anellovirus DNA is likely to represent only a minor fraction of the total DNA present in the sample.

A first approach that addresses these challenges is to sequence and quantify sequences which are known to be specific of the anellovirus genome. Indeed, the inventors have identified two consensus sequences, represented by SEQ ID No. 4 and SEQ ID No. 5, based on the comparison between all the anelloviral sequences. These two consensus sequences, which are capable of hybridizing to all the anelloviral genomes, are thus highly convenient as primers for sequencing the said anellovirus DNA.

Thus according to this embodiment, the method of the invention comprises using the primers of sequences represented by SEQ ID No. 4 and SEQ ID No. 5 for sequencing. In a preferred embodiment, the method of the invention comprises a step of quantifying the number of reads.

In yet a further preferred embodiment, the method of the invention comprises another further step of normalizing the said number of reads to a reference. The said reference may be any convenient DNA sequence which can be identified and quantified, e.g. a host DNA sequence or an exogenous sequence. It is particularly advantageous for quantitative sequencing to add ab initio into the samples a known amount of reference nucleic acids; which reference nucleic acids will pass through all sample preparation steps before sequencing. Sample preparation steps can comprise means to protect the viral nucleic acid and destroy host nucleic acids, for example using different nucleases.

Although the said primers can be used in solution, it is preferable that the said primers are linked to a solid support.

To permit its covalent coupling to the support, the primer is generally functionalized. Thus, it may be modified by a thiol, amine or carboxyl terminal group at the 5 ' or 3' position. In particular, the addition of a thiol, amine or carboxyl group makes it possible, for example, to couple the oligonucleotide to a support bearing disulphide, maleimide, amine, carboxyl, ester, epoxide, cyanogen bromide or aldehyde functions. These couplings form by establishment of disulphide, thioether, ester, amide or amine links between the primer and the support. Any other method known to a person skilled in the art may be used, such as bifunctional coupling reagents, for example.

Moreover, to improve the hybridization with the coupled oligonucleotide, it can be advantageous for the oligonucleotide to contain an "arm" and a "spacer" sequence of bases. The use of an arm makes it possible, in effect, to bind the primer at a chosen distance from the support, enabling its conditions of interaction with the DNA to be improved. The arm advantageously consists of a linear carbon chain, comprising 1 to 18 and preferably 6 or 12 ($CH_2$) groups, and an amine which permits binding to the column. The arm is linked to a phosphate of the oligonucleotide or of a "spacer" composed of bases which do not interfere with the hybridization. Thus, the "spacer" can comprise purine bases. As an example, the "spacer" can comprise the sequence GAGG. The arm is advantageously composed of a linear carbon chain comprising 6 or 12 carbon atoms.

For implementation of the present invention, different types of support may be used. These can be functionalized chromatographic supports, in bulk or prepacked in a column, functionalized plastic surfaces or functionalized latex beads, magnetic or otherwise. Chromatographic supports are preferably used. As an example, the chromatographic supports capable of being used are agarose, acrylamide or dextran as well as their derivatives (such as Sephadex, Sepharose, Superose, etc.), polymers such as poly(styrene/divinylbenzene), or grafted or ungrafted silica, for example. The chromatography columns can operate in the diffusion or perfusion mode.

Thus, in one particular embodiment, the above primers such as SEQ ID No 4 and 5, or primers featuring at least 12, 15, 20 or 25 consecutive bases of SEQ ID No 4 or 5, or other primers specific for anellovirus nucleic acids amplification, further comprise:

a functional group for covalent coupling at the 5' or 3' end such as but not limited to a group comprising a thiol, amine or carboxyl terminal group;

a spacer molecule or sequence is added at the 5' or 3' end, which spacer molecule or sequence is as featured above;

optionally, additional sequences as index or tag sequences to perform pre or post additional and general amplification steps not depending on the target sequences to be quantified.

Another approach is to use a method that allows the quantitative genotyping of nucleic acids obtained from the biological sample with high precision. In one embodiment of this approach, the precision is achieved by analysis of a large number (for example, millions or billions) of nucleic acid molecules without any amplification using protocols that relies on previous knowledge of the target sequences (i.e. in this case, anellovirus sequences). One embodiment uses massively parallel DNA sequencing, such as, but not limited to that performed by the Illumina Genome Analyzer platform (Bentley et al. *Nature;* 456: 53-59, 2008), the Roche 454 platform (Margulies et al. *Nature;* 437: 376-380, 2005), the ABI SOLiD platform (McKernan et al., *Genome Res;* 19: 1527-1541, 2009), the Helicos single molecule sequencing platform (Harris et al. *Science;* 320: 106-109, 2008), real-time sequencing using single polymerase molecules (*Science;* 323: 133-138, 2009), Ion Torrent sequencing (WO 2010/008480; Rothberg et al., Nature, 475: 348-352, 2011) and nanopore sequencing (Clarke J et al. *Nat Nanotechnol.;* 4: 265-270, 2009). In one embodiment, massively parallel sequencing is performed on a random subset of nucleic acid molecules in the biological sample.

In specific embodiments, the method and kit of the invention is adapted to run on ABI PRISM® 377 DNA Sequencer, an ABI PRISM® 310, 3100, 3100-Avant, 3730, or 3730x1 Genetic Analyzer, an ABI PRISM® 3700 DNA Analyzer, or an Applied Biosystems SOLiD™ System (all from Applied Biosystems), a Genome Sequencer 20 System (Roche Applied Science), an HiSeq 2500, an HiSeq 2000, a Genome Analyzer IIx, a MiSeq Personal Sequencer, a HiScanSQ (all from Illumina), the Genetic Analysis System, including the Single Molecule Sequencer, Analysis Engine and Sample Loader (all from HeliScope), the Ion Proton™ Sequencer, or the Ion PGM™ Sequencer (both from Ion Torrent). In a preferred embodiment of the invention, anellovirus sequences are identified in the global sequencing data by comparison with the publicly-deposited anellovirus sequences. This comparison is advantageously based on the level of sequence identity with a known anellovirus sequence and allow to detect even distant variants.

The term "sequence identity" refers to the identity between two peptides or between two nucleic acids. Identity between sequences can be determined by comparing a position in each of the sequences which may be aligned for the purposes of comparison. When a position in the compared sequences is occupied by the same base or amino acid, then the sequences are identical at that position. A degree of sequence identity between nucleic acid sequences is a function of the number of identical nucleotides at positions shared by these sequences. A degree of identity between amino acid sequences is a function of the number of identical amino acid sequences that are shared between these sequences. Since two polypeptides may each (i) comprise a sequence (i.e. a portion of a complete polynucleotide sequence) that is similar between two polynucleotides, and (ii) may further comprise a sequence that is divergent between two polynucleotides, sequence identity comparisons between two or more polynucleotides over a "comparison window" refers to the conceptual segment of at least 20 contiguous nucleotide positions wherein a polynucleotide sequence may be compared to a reference nucleotide sequence of at least 20 contiguous nucleotides and wherein the portion of the polynucleotide sequence in the comparison window may comprise additions or deletions (i.e. gaps) of 20 percent or less compared to the reference sequence (which does not comprise additions or deletions) for optimal alignment of the two sequences.

To determine the percent identity of two amino acids sequences or two nucleic acid sequences, the sequences are aligned for optimal comparison. For example, gaps can be introduced in the sequence of a first amino acid sequence or a first nucleic acid sequence for optimal alignment with the second amino acid sequence or second nucleic acid sequence. The amino acid residues or nucleotides at corresponding amino acid positions or nucleotide positions are then compared. When a position in the first sequence is occupied by the same amino acid residue or nucleotide as the corresponding position in the second sequence, the molecules are identical at that position. The percent identity between the two sequences is a function of the number of identical positions shared by the sequences. Hence % identity=number of identical positions/total number of overlapping positions×100.

In this comparison the sequences can be the same length or can be different in length. Optimal alignment of sequences for determining a comparison window may be conducted by the local homology algorithm of Smith and Waterman (*J. Theor. Biol.*, 91(2): 370-380, 1981), by the homology alignment algorithm of Needleman and Wunsch (*J. Mol. Biol*, 48(3): 443-453, 1972), by the search for similarity via the method of Pearson and Lipman (*Proc. Natl. Acad. Sci. U.S.A.*, 85(5): 2444-2448, 1988), by computerized implementations of these algorithms (GAP, BESTFIT, FASTA and TFASTA in the Wisconsin Genetics Software Package Release 7.0, Genetic Computer Group, 575, Science Drive, Madison, Wisconsin) or by inspection. The best alignment (i.e. resulting in the highest percentage of identity over the comparison window) generated by the various methods is selected.

The term "sequence identity" thus means that two polynucleotide or polypeptide sequences are identical (i.e. on a nucleotide by nucleotide or an amino acid by amino acid basis) over the window of comparison. The term "percentage of sequence identity" is calculated by comparing two optimally aligned sequences over the window of comparison, determining the number of positions at which the identical nucleic acid base (e.g. A, T, C, G, U, or I) occurs in both sequences to yield the number of matched positions, dividing the number of matched positions by the total number of positions in the window of comparison (i.e. the window size) and multiplying the result by 100 to yield the percentage of sequence identity. The same process can be applied to polypeptide sequences. The percentage of sequence identity of a nucleic acid sequence or an amino acid sequence can also be calculated using BLAST software (Version 2.06 of September 1998) with the default or user defined parameter.

Thus, a sequence displaying at least 80%, at least 85%, at least 90%, at least 95%, at least 96%, at least 97%, at least 98%, at least 99%, or 100% identity with a known anellovirus sequence is identified as an anellovirus sequence.

According to this embodiment, determining the anelloviral load thus includes numbering the anellovirus sequences identified by sequencing in the biological sample of the subject.

In a preferred embodiment, the levels of anellovirus DNA are determined by measuring the number of anellovirus DNA sequences present in the biological sample.

In a further preferred embodiment, the number of anelloviral sequences is normalized to the total number of sequences identified by sequencing in the biological sample. By "normalizing to the total number of sequences", it is herein meant that the number of anelloviral sequences is divided by the total number of sequences, i.e. both from anelloviral and non-anelloviral origin, present in the biological sample. According to this embodiment, a ratio of anelloviral sequences to total sequences higher than $0.2 \times 10^{-4}$ indicates that the subject is immunosuppressed. In a yet further preferred embodiment, the subject is immunosuppressed if the said ratio is higher than $0.5 \times 10^{-4}$, higher than $1 \times 10^{-4}$, higher than $5 \times 10^{-4}$, higher than $10 \times 10^{-4}$, higher than $15 \times 10^{-4}$, higher than $20 \times 10^{-4}$, higher than $25 \times 10^{-4}$, or higher than $25 \times 10^{-4}$.

In another embodiment, determining the anelloviral load further includes the steps of assigning each anellovirus sequence identified by sequencing to a specific anellovirus genome and numbering the copies of anellovirus genomes thus identified. By assigning a sequence to a specific anellovirus genome, it is herein meant the process of identifying the anellovirus genome to which the said sequence belongs. Advantageously, this process is carried out by comparison of the said sequence with the anelloviral sequences deposited in public databases.

By "anellovirus genomes", it is herein referred to the genomes of any virus belonging to the Anelloviridae family of viruses, comprising Torque Teno viruses (TTVs), Torque Teno midiviruses (TTMDVs), Torque Teno miniviruses also formerly known as Torque Teno-like miniviruses (TTMVs).

In an embodiment, it is referred to TTVs genomes, comprising alphatorqueviruses, betatorqueviruses, gammatorqueviruses, deltatorqueviruses, epsilontorqueviruses, etatorqueviruses, iotatorqueviruses, thetatorqueviruses, zetatorqueviruses. In a preferred embodiment, it is referred to the genome of the prototype strain of Torque Teno virus, TTV-1a. An example of a TTV genome is a sequence such as in e.g. Genebank accession number AB017610 and represented in SEQ ID No 1.

In another embodiment, it is referred to TTMDVs genomes. In a preferred embodiment, it is referred to the genome of the prototype strain of Torque Teno midiviruses, namely the genome of the MD1-073 isolate. For example, a TTMDV genome may have a sequence such as in e.g. Genbank accession number AB290918 and represented in SEQ ID No 2.

In another embodiment, it is referred to TTMVs genomes. In a preferred embodiment, it is referred to the genome of the prototype strain of Torque Teno miniviruses, namely the genome of TTMV-NLC-030 isolate. A TTMV genome is illustrated by a sequence such as in e.g. Genbank accession number AB038631 and represented in SEQ ID No 3.

It is possible to normalize the number of anellovirus genomes to at least one sequence, in order to reduce the error rate when comparing the anelloviral loads of two distinct biological samples. By "normalizing to a sequence", it is herein meant that the number of anellovirus genomes identified in the biological sample is divided by the number of copies of the said sequence. The said sequence can be for example a non-human sequence whose copy number is known. Alternatively, the said sequence is a human sequence. Preferably, number of anellovirus genomes is normalized to the whole human genome. By "human genome" it is herein referred to a consensus sequence of reference, such as the sequence corresponding to Genome Reference Consortium built GRCh37 (NCBI build 37.1/assembly hg19).

In a preferred embodiment, the ratio of anellovirus genomes to human genome is higher than 0.2%.

Alternatively, the number of anelloviral sequences in a given sample is compared to an internal control. The said internal control enables the assessment of the quality and the extent of the sequencing of the nucleic acid molecules in the said sample. Preferably, the said internal control consists of a nucleic acid molecule having a known sequence, said nucleic acid molecule being present in the said sample at a known concentration. More preferably, the said nucleic acid molecule is the genomic single-stranded circular DNA molecule of a virus of known sequence and concentration in the said sample. Such a known virus may be e.g. a virus of the Circoviridae family. The ratio of the number of sequences of the sample to the control allows estimating the absolute number of anelloviral genomes of known sequence and concentration.

In another embodiment, amplification techniques are used to determine the anelloviral load. Such amplification techniques include in particular isothermal methods and PCR-based techniques. Isothermal techniques include such methods as e.g. nucleic acid sequence-based amplification (NASBA), loop-mediated isothermal amplification (LAMP), helicase-dependent amplification (HDA), rolling circle amplification (RCA), and strand displacement amplification (SDA), exponential amplification reaction (EX-PAR), isothermal and chimeric primer-initiated amplification of nucleic acids (ICANs), signal-mediated amplification of RNA technology (SMART) and others (see e.g. Asiello and Baeumner, Lab Chip; 11(8): 1420-1430, 2011). Preferably, the PCR technique used quantitatively measures starting amounts of DNA, cDNA, or RNA. Examples of PCR-based techniques according to the invention include techniques such as, but not limited to, quantitative PCR (Q-PCR), reverse-transcriptase polymerase chain reaction (RT-PCR), quantitative reverse-transcriptase PCR (QRT-PCR), or digital PCR. These techniques are well known and easily available technologies for those skilled in the art and do not need a precise description.

In a preferred embodiment, the determination of anelloviral load is performed by quantitative PCR.

In another preferred embodiment, the determination of the adenoviral load is performed by digital PCR. Digital PCR involves multiple PCR analyses on extremely dilute nucleic acids such that most positive amplifications reflect the signal from a single template molecule. Digital PCR thereby permits the counting of individual template molecules. The proportion of positive amplifications among the total number of PCRs analyzed allows an estimation of the template concentration in the original or non-diluted sample. This technique has been proposed to allow the detection of a variety of genetic phenomena (Vogelstein et al., Proc Natl Acad Sci USA 96: 9236-924, 1999). Since template molecule quantification by digital PCR does not rely on dose-response relationships between reporter dyes and nucleic acid concentrations, its analytical precision is, at least theoretically, superior to that of real-time PCR. Hence, digital PCR potentially allows the discrimination of finer degrees of quantitative differences between target and reference loci.

In another embodiment, the method of the invention comprises a further step (a') of comparing the anelloviral load of step (a) to at least one reference anelloviral load. According to this embodiment, the determination of the immunosuppressed or non-immunosuppressed phenotype is carried out thanks to the obtained anelloviral load with at least one reference anelloviral load in step (a').

According to the invention, the "reference anelloviral load" is a predetermined measure of anelloviral load, obtained from a biological sample from a subject with a known immune status. Preferably, the reference anelloviral load is predetermined measure of anelloviral load, obtained from a biological sample from a subject with a known immunosuppressed status. In a preferred embodiment, the reference anelloviral load is predetermined measure of anelloviral load, obtained from a biological sample from a subject known to be immunosuppressed. In another embodiment, the reference anelloviral load is predetermined measure of anelloviral load, obtained from a biological sample from a subject known not to be immunosuppressed.

Preferably, at least one reference expression profile is an immunosuppressed reference anelloviral load. Alternatively, at least one reference anelloviral load may be a non-immunosuppressed reference anelloviral load. More preferably, the determination of the presence or absence of an immunosuppressed phenotype is carried out by comparison with at least one immunosuppressed and at least one non-immunosuppressed reference anelloviral load. The diagnosis or prognostic may thus be performed using one immunosuppressed reference anelloviral load and one non-immunosuppressed reference anelloviral load. Advantageously, to get a stronger diagnosis or prognostic, said diagnosis or prognostic is carried out using several immunosuppressed reference anelloviral loads and several non-immunosuppressed reference anelloviral loads.

According to the invention, any sequence of the anellovirus genome may be targeted for amplification in order to determine the anelloviral load. The said sequence may be conserved amongst the viral strains or it may be only present in a specific group of strains. In the latter case, it is necessary to amplify as well another sequence present in the other groups of anellovirus strains. Preferably, the amplified anellovirus sequence is conserved among the Anelloviridae family, in which case a single set of primers may be used to amplify, in a single reaction, all the viral strains present in the biological sample. More preferably, more than one conserved sequences in the Anelloviridae family are amplified, thus increasing the sensitivity of the test.

In a specific embodiment, a reference sequence is also targeted for amplification, and used as a control or as a standard. Preferably, this reference sequence is chosen within the human genome.

In a preferred embodiment, the determination of anelloviral load is performed using Q-PCR; at least one consensus sequence of anellovirus genome is targeted for amplification.

The primers are chosen by the skilled in the art depending on the desired specificity of the PCR amplification step using standard parameters such as the nucleic acid size, GC contents, and temperature reactions.

In a more preferred embodiment, any anelloviral sequence comprised between the consensus sequences represented by SEQ ID No. 4 and SEQ ID No. 5 is targeted for amplification. Even more preferably, the anelloviral sequence comprised between the consensus sequences represented by SEQ ID No. 4 and SEQ ID No. 5 is targeted for amplification.

The present inventors have identified two consensus sequences, represented by SEQ ID No. 4 and SEQ ID No. 5, based on the comparison between all the anelloviral sequences. Preferably, when amplification is performed, amplification primers comprise any primers capable of binding to a polynucleotide having said consensus sequences SEQ ID No. 4 or SEQ ID No. 5, with the proviso that the said primers are different from SEQ ID No. 6 and SEQ ID No. 7. In a specific embodiment, the said primers comprise between 10 and 30 nucleotides, preferably between 15 and 25 nucleotides, more preferably between 20 and 25 nucleotides. More preferably, the said primers comprise at least 12, 15, 20 or 25 bases of SEQ ID No. 4 or 5. Parameters for determining the exact primer sequence on the basis of the target sequence are well known to the person of skills in the art.

Although the said primers can be used in solution, it is preferable that the said primers are linked to a solid support.

To permit its covalent coupling to the support, the primer is generally functionalized. Thus, it may be modified by a thiol, amine or carboxyl terminal group at the 5' or 3' position. In particular, the addition of a thiol, amine or carboxyl group makes it possible, for example, to couple the oligonucleotide to a support bearing disulphide, maleimide, amine, carboxyl, ester, epoxide, cyanogen bromide or aldehyde functions. These couplings form by establishment of disulphide, thioether, ester, amide or amine links between the primer and the support. Any other method known to a person skilled in the art may be used, such as bifunctional coupling reagents, for example.

Moreover, to improve the hybridization with the coupled oligonucleotide, it can be advantageous for the oligonucleotide to contain an "arm" and a "spacer" sequence of bases. The use of an arm makes it possible, in effect, to bind the primer at a chosen distance from the support, enabling its conditions of interaction with the DNA to be improved. The arm advantageously consists of a linear carbon chain, comprising 1 to 18 and preferably 6 or 12 ($CH_2$) groups, and an amine which permits binding to the column. The arm is linked to a phosphate of the oligonucleotide or of a "spacer" composed of bases which do not interfere with the hybridization. Thus, the "spacer" can comprise purine bases. As an example, the "spacer" can comprise the sequence GAGG. The arm is advantageously composed of a linear carbon chain comprising 6 or 12 carbon atoms.

For implementation of the present invention, different types of support may be used.

These can be functionalized chromatographic supports, in bulk or prepacked in a column, functionalized plastic surfaces or functionalized latex beads, magnetic or otherwise. Chromatographic supports are preferably used. As an example, the chromatographic supports capable of being used are agarose, acrylamide or dextran as well as their derivatives (such as Sephadex, Sepharose, Superose, etc.), polymers such as poly(styrene/divinylbenzene), or grafted or ungrafted silica, for example. The chromatography columns can operate in the diffusion or perfusion mode.

In another embodiment of the invention, the quantity of anellovirus DNA is determined using sequence specific hybridization. The terms "hybridization" and "hybridizing" refers to the pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used.

The probes are chosen by the person skilled in the art depending on the desired specificity of the specificity of the detection step using standard parameters such as the nucleic acid size and GC contents, stringent hybridization conditions and temperature reactions. For example, low stringency conditions are used when it is desired to obtain broad positive results on a range of homologous targets whereas high stringency conditions are preferred to obtain positive results only if the specific target nucleic is present in the sample.

Preferably, the probe of the invention is capable of hybridizing with a polynucleotide having a sequence represented by SEQ ID No. 4 or SEQ ID No. 5, with the proviso that the said probe does not have a sequence represented by SEQ ID No. 6 or SEQ ID No. 7. It is another aspect of the invention to provide a polynucleotide comprising at least 12, 15, 20 or consecutive bases represented by SEQ ID No. 4 or SEQ ID No. 5.

The hybridizing probes may be labeled with a radioactive marker, a fluorescent marker, or a chemical marker. Branched DNA (bDNA), involves oligonucleotides with branched structures that allow each individual oligonucleotide to carry 35 to 40 labels (e.g., alkaline phosphatase enzymes). These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences. Such methods of hybridization of a labeled probe with a DNA molecule are well known to the person of skills in the art. For example, low stringency conditions are used when it is desired to obtain broad positive results on a range of homologous targets whereas high stringency conditions are preferred to obtain positive results only if the specific target nucleic is present in the sample. As used herein, the term "stringent hybridization conditions" refers to conditions under which the probe will hybridize only to that exactly complementary target sequence, and which allow the detection of the specific target sequence. The hybridization conditions affect the stability of hybrids, e.g., temperature, salt concentration, pH, formamide concentration and the like. These conditions are optimized to maximize specific binding and minimize non-specific binding of primer or probe to its target nucleic acid sequence. Stringent conditions are sequence dependent and will be different in different circumstances. Longer sequences hybridize specifically at higher temperatures. Generally, stringent conditions are selected to be about 5° C. lower than the thermal melting point (Tm) for the specific sequences at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M Nat, typically about 0.01 to 1.0 M Na' concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions include hybridization with a buffer solution of 20-30% formamide, 1 M NaCl, 1% SDS at 37° C. and a wash in 2×SSC at 40° C. Exemplary high stringency conditions include hybridization in 40-50% formamide, 1 M NaCl, 1% SDS at 37° C., and a wash in 0.1*SSC at 60° C. Determination of particular hybridization conditions relating to a specified nucleic acid is routine and is well known in the art, for instance, as described in Sambrook and Russell, Molecular Cloning: A Laboratory Manual, Cold Spring Harbor Laboratory Press; 3rd Ed., 2001; and Ausubel, Ed., Short Protocols in Molecular Biology, Current Protocols; 5th Ed., 2002.

In a preferred embodiment, the anelloviral load is determined by the use of a nucleic microarray.

According to the invention, a "nucleic microarray" consists of different nucleic acid probes that are attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes can be nucleic acids such as cDNAs ("cDNA microarray") or oligonucleotides ("oligonucleotide microarray"), and the oligonucleotides may be about 25 to about 60 base pairs or less in length.

To determine the amount of a target nucleic sample, said sample is labelled, contacted with the microarray in hybridization conditions, leading to the formation of complexes between target nucleic acids that are complementary to probe sequences attached to the microarray surface. The presence of labelled hybridized complexes is then detected. Many variants of the microarray hybridization technology are available to the man skilled in the art.

The practice of the invention employs, unless other otherwise indicated, conventional techniques or protein chemistry, molecular virology, microbiology, recombinant DNA technology, and pharmacology, which are within the skill of the art. Such techniques are explained fully in the literature. (See Ausubel et al., Short Protocols in Molecular Biology, Current Protocols; 5th Ed., 2002; Remington's Pharmaceutical Sciences, 17th ed., Mack Publishing Co., Easton, Pa., 1985; and Sambrook et al., Molecular Cloning: A Laboratory Manual, Cold Spring Harbor Laboratory Press; 3rd Ed., 2001). The nomenclatures used in connection with, and the laboratory procedures and techniques of, molecular and cellular biology, protein biochemistry, enzymology and medicinal and pharmaceutical chemistry described herein are those well-known and commonly used in the art.

The following examples are provided herein for purposes of illustration only and are not intended to be limiting unless otherwise specified.

EXAMPLES

Example 1

ANV as a Marker of Immune Suppression

We have screened plasma samples from patients suffering from various forms of congenital immune suppression and from patients without any known immunosuppression: the extraction procedure was optimized for isolation of viral DNA or RNA genomes without precluding identification of bacterial and fungal nucleic acids. A volume of 150 µl of each sample was extracted using the Nucleospin RNA virus kit (Macherey-Nagel), which allows recovery of both DNA and RNA, and then amplified by the bacteriophage phi29 polymerase based multiple displacement amplification (MDA) assay using random primers.

This technique allows DNA synthesis from DNA samples, and also from cDNA fragments from viral genomes previously colligated prior to Phi29 polymerase-MDA.

Briefly, the protocol of the QuantiTect Whole Transcriptome Kit (Qiagen) was followed, except that the cDNA synthesis step was performed with random hexamer primers.

A mix with 8 µl of RNA, 1 µl of primer (50 µM) and 1 µl of dNTPs (10 mM) was incubated at 75° C. for 5 min and cooled on ice for 5 min.

Then, 10 µl of 2× enzyme mix were added. This enzyme mix was composed of 2 µl of 10× RT Buffer for SSIII (Invitrogen Inc.), 4 µl of 25 mM MgCl$_2$, 2 µl µL of 0.1 M DTT, 1 µl µL of 40 U/µl RNaseOUT (Invitrogen Inc.), 1 µl of SuperScript III reverse transcriptase (Invitrogen Inc.) and 0.5 µl of DMSO (Sigma-Aldrich).

The final mix was incubated at 25° C. for 10 min, then at 45° C. for 90 min and finally at 95° C. for 5 min.

All cDNAs were stored at −20° C. or immediately used.

The two following steps (ligation and WGA) were performed with the QuantiTect® Whole Transcriptome kit (Qiagen) according to the manufacturer's instructions.

This provides concatemers of high molecular weight DNA.

High molecular weight DNA (5 µg), resulting from isothermal amplification of the pool of genomic DNAs and cDNAs made from genomic RNAs as described above, was fragmented into 200 to 350 nt fragments, to which adapters were ligated. Adapters included a nucleotide tag allowing for multiplexing several samples per lane or channel. Sequencing was conducted on an Illumina GAIT or HiSeq 2000 sequencer.

Sorting out the flow of Illumina sequences was first done by a subtractive database comparison procedure. To this end, the whole human genome sequence (NCBI build 37.1/assembly hg19) was scanned with the reads using SOAPaligner. A quick and very restrictive BLASTN study was also performed to eliminate additional host reads. The best parameters to be used have been determined previously. A number of assembly programs dedicated to short or medium-sized reads (Velvet, SOAPdenovo, CLC) have been tested for their efficiency in our pipeline. Optimal parameters have been set. The comparison of the single reads and contigs with already known genomic and taxonomic data was done on dedicated specialized viral, bacterial and generalist databases maintained locally (GenBank viral and bacterial databases, nr). The aforementioned databases were scanned using BLASTN and BLASTX. Binning (or taxonomic assignment) was based on the lowest common ancestor or from the best hit, identified from the best hits among single reads or contigs with a significant e-value.

Results regarding single reads with e-values below $10^{-4}$ that had a best match for a known member of the Anelloviridae family (ANV) are shown in table 1.

As shown in table 1, we have identified ANV reads in 14/14 immunodeficient patients. Interestingly, for a subset of three patients characterized with a major immune T-cell suppression, 20 to 54% of the total number of reads were anellovirus reads. On the contrary, other immune compromised patients that showed lower immunosuppression states depicted <0.2% anellovirus virus reads.

In 34 patients not known to be immune-compromised, no read (or less than 5 reads) was identified except in a set of four patients: three of them (100036,100039, 080114/116) were developing an encephalitis at the time of sampling, a medical condition frequently associated with immune suppression.

TABLE 1

Number of single reads or of reads assembled in contigs identified for patients with immunosuppression or without known immunosuppression.

| Code | Sample | Immunosuppression state | number of reads | anellovirus reads | ratio anello/total ($\times 10^{-4}$) |
|---|---|---|---|---|---|
| KNOWN IMMUNOSUPPRESSSION ||||||
| 100023 | Plasma | SCID gamma C/hepatitis | 5 132 262 | 191 | 0.37 |
| 100025 | Plasma | SCID/HPV infections | 5 345 602 | 2 889 856 | 5406.04 |
| 100026 | Plasma | Bruton's Agammaglobulinemia | 3 091 732 | 94 | 0.30 |
| 100028 | Plasma | SCID gamma C/encephalopathy | 3 506 376 | 13 | 0.04 |
| 100029 | Plasma | Severe lymphopenia | 6 467 110 | 3 299 612 | 5102.14 |
| 100030 | Plasma | Atypical Still disease/ fever of unknown origin | 12 029 412 | 13 | 0.01 |
| 100031 | Plasma | Septic granulomatosis | 2 770 398 | 2 871 | 10.36 |
| 100061 | Plasma | Severe lymphopenia | 9 184 316 | 526 | 0.57 |
| 100081 | Plasma | Griscelli disease and CMV infection | 8 540 162 | 5 272 | 6.17 |
| 100082 | Cerebrospinal Fluid | SCID Rag1 | 20 875 934 | 1 805 | 0.86 |
| 100083 | Plasma | Severe lymphopenia | 9 643 096 | 16 129 | 16.73 |
| 100084 | Plasma | Severe lymphopenia | 8 128 858 | 1 705 998 | 2098.69 |
| 100085 | Plasma | leukemia | 6 410 912 | 286 | 0.45 |
| 100243 | Skin swab | Severe lymphopenia | 39 942 410 | 132 761 | 33.24 |
| CONTROLS ||||||
| 100036 | Plasma | NIL | 13 564 262 | 187 | 0.14 |
| 100039 | Plasma | NIL | 6 071 374 | 915 | 1.51 |
| 080114/116 | Plasma | NIL | 9 633 342 | 164 | 0.17 |
| 100053 | Plasma | NIL | 7 375 016 | 0 | 0.00 |
| 100032 | Plasma | NIL | 7 148 184 | 0 | 0.00 |
| 100033 | Plasma | NIL | 3 348 242 | 4 | 0.01 |
| 100034 | Plasma | NIL | 14 198 534 | 0 | 0.00 |
| 100035 | Plasma | NIL | 13 905 700 | 0 | 0.00 |
| 100037 | Plasma | NIL | 13 784 866 | 0 | 0.00 |
| 100038 | Plasma | NIL | 27 941 897 | 0 | 0.00 |
| 100062 | Plasma | NIL | 12 098 932 | 2 | 0.00 |
| 100063 | Plasma | NIL | 8 701 704 | 1 | 0.00 |
| 100064 | Plasma | NIL | 7 976 148 | 0 | 0.00 |
| 100066 | Plasma | NIL | 8 052 770 | 156 | 0.19 |
| 100067 | Plasma | NIL | 10 354 496 | 2 | 0.00 |
| 100069 | Plasma | NIL | 9 107 144 | 0 | 0.00 |
| 100070 | Plasma | NIL | 8 196 240 | 2 | 0.00 |
| 100072 | Plasma | NIL | 7 588 712 | 0 | 0.00 |
| 100073 | Plasma | NIL | 10 281 130 | 0 | 0.00 |
| 100192 | Plasma | NIL | 28 726 064 | 0 | 0.00 |
| 100236 | Plasma | NIL | 4 818 410 | 0 | 0.00 |
| 100237 | Plasma | NIL | 6 047 999 | 0 | 0.00 |
| 100238 | Plasma | NIL | 4 742 180 | 0 | 0.00 |
| 100239 | Plasma | NIL | 4 837 188 | 0 | 0.00 |
| 100240 | Plasma | NIL | 5 281 443 | 0 | 0.00 |
| 100241 | Plasma | NIL | 9 226 049 | 0 | 0.00 |

Example 2

Identification of Conserved Sequences Among ANVs Genomes

An ANV sequence database was built. It was composed by 7,003 nucleotide sequences assigned to the Anelloviridae family. 6938 sequences come from the NCBI public database (NT, Oct. 1, 2011). 65 sequences come from de novo assembly of NGS reads derived from our own work (see table 1) that were assigned to the Anelloviridae family. These sequences have a minimal length of 1000 nucleotides.

In a preliminary analysis using a short set of sequences, sequences that are close to a transcriptional factor binding site (called TATA box) seemed conserved among strains. To further extend this analysis, and in order to reduce the database size, filter based on the presence of the TATA box was performed. This motif is A/T rich and was located upstream of the transcription start site.

A consensus sequence of the TATA box was built, using the following sequences: ATAAAA, ATAAAT, ATATAA, ATATAT.

This motif was used as an anchor in order to:
1. Filter the anellovirus database. A search with a position specific weight matrix was performed with this consensus. Sequence without an exact match was discarded.
2. Pre-aligned long nucleotide sequences. Previously selected sequences were aligned at the beginning of the TATA consensus (+1).

This filtering step reduced the database to:
42 sequences obtained from the NCBI.
8 sequences obtained from our own NGS runs and de novo assembly.

A second alignment was done with MUSCLE (default parameters). Two conserved regions were identified at position [+20: +53] and position [+121: +151] relative to the TATA box consensus.

Details of these alignments are shown below. Each line corresponds to a specific nucleotide position. Columns represent respectively the A, C, G and T counts at this position. Lines with a star correspond to a well-conserved position. Nucleotide ambiguity was shown using bracket. The last column is the consensus nucleotide at each position using the IUAPAC nomenclature.

TABLE 2

IUAPAC Nomenclature

| Nucleotide Code | Base |
|---|---|
| A | Adenine |
| C | Cytosine |
| G | Guanine |
| T (or U) | Thymine (or Uracil) |
| R | A or G |
| Y | C or T |
| S | G or C |
| W | A or T |
| K | G or T |
| M | A or C |
| B | C or G or T |
| D | A or G or T |
| H | A or C or T |
| V | A or C or G |
| N | any base |
| or - | gap |

• First region: ANV-PTQ-1

| A | C | G | T | | | |
|---|---|---|---|---|---|---|
| 0 | 0 | 50 | 0 | * | G | G |
| 50 | 0 | 0 | 0 | * | A | A |
| 50 | 0 | 0 | 0 | * | A | A |
| 0 | 0 | 0 | 50 | * | T | T |
| 0 | 0 | 50 | 0 | * | G | G |
| 0 | 0 | 50 | 0 | * | G | G |
| 0 | 37 | 0 | 13 | | [CT] | Y |
| 13 | 0 | 0 | 37 | | [AT] | W |
| 0 | 0 | 50 | 0 | * | G | G |
| 50 | 0 | 0 | 0 | * | A | A |
| 0 | 0 | 50 | 0 | * | G | G |
| 0 | 0 | 0 | 50 | * | T | T |
| 0 | 0 | 0 | 50 | * | T | T |
| 0 | 0 | 0 | 50 | * | T | T |
| 0 | 2 | 0 | 11 | | [CT] | Y |
| 14 | 0 | 0 | 36 | | [AT] | W |
| 0 | 36 | 0 | 14 | | [CT] | C |
| 0 | 24 | 14 | 12 | | [CGT] | B |
| 23 | 14 | 0 | 13 | | [ACT] | H |
| 0 | 49 | 1 | 0 | | C | C |
| 0 | 0 | 50 | 0 | * | G | G |
| 0 | 50 | 0 | 0 | * | C | C |
| 10 | 37 | 0 | 3 | | [AC] | C |
| 2 | 35 | 12 | 1 | | [CG] | S |
| 0 | 0 | 50 | 0 | * | G | G |
| 4 | 0 | 0 | 36 | | [AT] | T |
| 0 | 38 | 0 | 12 | | [CT] | Y |
| 0 | 36 | 14 | 0 | | [CG] | S |
| 0 | 0 | 50 | 0 | * | G | G |
| 0 | 36 | 0 | 12 | | [CT] | Y |
| 36 | 0 | 14 | 0 | | [AG] | R |
| 0 | 0 | 50 | 0 | * | G | G |
| 18 | 1 | 0 | 0 | | [AT] | A |

• Second region: ANV-PTQ-2

| A | C | G | T | | | |
|---|---|---|---|---|---|---|
| 50 | 0 | 0 | 0 | * | A | A |
| 0 | 38 | 12 | 0 | | [CG] | S |
| 0 | 50 | 0 | 0 | * | C | C |
| 0 | 0 | 50 | 0 | * | G | G |
| 16 | 21 | 12 | 1 | | [ACG] | V |
| 50 | 0 | 0 | 0 | * | A | A |
| 0 | 0 | 50 | 0 | * | G | G |
| 0 | 0 | 0 | 50 | * | T | T |
| 0 | 50 | 0 | 0 | * | C | C |
| 49 | 0 | 0 | 1 | * | A | A |
| 50 | 0 | 0 | 0 | * | A | A |
| 0 | 0 | 50 | 0 | * | G | G |
| 0 | 0 | 50 | 0 | * | G | G |
| 0 | 0 | 50 | 0 | * | G | G |
| 0 | 50 | 0 | 0 | * | C | C |
| 38 | 10 | 0 | 2 | | [AC] | M |
| 38 | 0 | 0 | 12 | | [AT] | W |
| 12 | 0 | 0 | 38 | | [AT] | W |
| 0 | 0 | 0 | 50 | * | T | T |
| 0 | 50 | 0 | 0 | * | C | C |
| 0 | 0 | 50 | 0 | * | G | G |
| 0 | 0 | 50 | 0 | * | G | G |
| 0 | 0 | 50 | 0 | * | G | G |
| 0 | 50 | 0 | 0 | * | C | C |
| 16 | 0 | 10 | 24 | | [AGT] | D |
| 2 | 36 | 12 | 0 | | [CG] | S |
| 0 | 0 | 50 | 0 | * | G | G |
| 1 | 12 | 37 | 0 | | [CG] | S |
| 0 | 0 | 10 | 4 | | [GT] | K |
| 1 | 12 | 37 | 0 | | [CG] | S |
| 0 | 0 | 10 | 4 | | [GT] | G |
| 0 | 2 | 12 | 0 | | G | G |
| 2 | 2 | 0 | 10 | | T | T |
| 12 | 0 | 37 | 0 | | [AG] | R |
| 46 | 0 | 0 | 3 | | A | A |

The present inventors have thus identified the two following consensus sequences which are conserved among anelloviral strains.

ANV-PTQ-2
(SEQ ID No. 4)
5' ASCGVAGTCAAGGGGCMWWTCGGGCDSGSKSGGTRA 3'

ANV-PTQ-1
(SEQ ID No. 5)
5' GAATGGYWGAGTTTYWCBHCGCCSGTYSGYRGA 3'

Thus, primers can be defined within the following sequences and be used to develop PCRs so as to evidence a wide range of ANVs genome.

Example 3

At least 50 and up to 200 immunocompromized patients from hospital Necker (Paris) suffering from an infectious disease are enrolled. Immunosuppression in these patients is either due to a congenital defect, to immunosuppressive treatments post solid organ or bone marrow transplantation, or to evolution of a cancer.

High throughput sequencing is conducted on the plasma of each patient to evaluate the etiology of the disease and the anellovirus load as a potential marker of immunosuppression. The number of reads specific to anelloviruses is quantified and correlated with the immunosuppression level of each patient and with the progression of the disease.

Non immunocompromized patients serve as controls.

It is observed that high loads in anellovirus in patients correlate with increased immunosuppression.

The invention claimed is:

1. A method, comprising:
   1) obtaining a biological sample from a human subject who is or is suspected of being immunosuppressed; and
   2) measuring the number of anellovirus DNA sequences in the sample by a method comprising detecting Torque teno virus (TTV) DNA, Torque teno midi virus (TTMDV) DNA, and Torque teno mini virus (TTMV) DNA, wherein measuring the number of anellovirus DNA sequences in the sample comprises at least one amplification step or sequencing step with a primer comprising at least 15 consecutive bases of SEQ ID NO: 4 or SEQ ID NO: 5, with the proviso that the primer does not have the sequence of SEQ ID No. 6 or SEQ ID No. 7, using a nucleic acid amplification instrument and/or a sequencing instrument;
   3) measuring the number of total DNA sequences in the sample, wherein measuring the number of total DNA sequences in the sample comprises using a nucleic acid amplification instrument and/or a sequencing instrument; and
   4) generating a ratio of the measured number of anellovirus DNA sequences in the sample to the measured number of total DNA sequences in the sample, wherein the ratio of the measured number of anellovirus DNA sequences in the sample to the measured number of total DNA sequences in the sample is higher than $0.2 \times 10^{-4}$ in the sample;
   responsive to measuring the ratio at higher than $0.2 \times 10^{-4}$, determining that the human subject is immunosuppressed.

2. The method of claim 1, wherein said human subject suffers from transplant rejection.

3. The method of claim 1, wherein said human subject suffers from an infection.

4. The method of claim 1, wherein the number of anellovirus DNA sequences is measured by hybridization with a labeled probe, PCR amplification or sequencing.

5. The method of claim 1, wherein the number of anellovirus DNA sequences is measured by sequencing said anellovirus DNA.

6. The method of claim 1, wherein the number of anellovirus DNA sequences is measured by a method comprising at least one amplification step with primers comprising at least 15 consecutive bases of SEQ ID NO: 4 or 5.

7. The method of claim 6 wherein said primers further comprise at least one of:
   a functional group for covalent coupling at the 5' or 3' end,
   a spacer molecule or sequence at the 5' or 3' end,
   additional sequences as index or tag sequences to perform pre or post additional and general amplification steps not depending on the target sequences to be quantified.

8. The method of claim 1, wherein the number of anellovirus DNA sequences is measured by massive parallel sequencing.

9. The method of claim 1, wherein measuring the number of anellovirus DNA sequences in the sample further comprises the steps of assigning each anellovirus sequence to a specific anellovirus genome and numbering the copies of anellovirus genomes thus identified.

10. The method of claim 1, wherein the number of anellovirus DNA sequences in the sample is determined by quantitative PCR.

11. The method of claim 1, wherein measuring the number of anellovirus DNA sequences in the sample comprises the amplification of at least one consensus anellovirus sequence.

12. The method of claim 7 wherein said functional group for covalent coupling at the 5' or 3' end is a terminal group comprising a thiol, amine or carboxyl group.

13. The method of claim 1, wherein determining that the human subject is immunosuppressed further comprises determining a degree of immunosuppression for the subject.

14. A method of preparing a value indicative of an immunosuppressed status in a human subject who is or is suspected of being immunosuppressed, comprising:
   1) obtaining a biological sample from the human subject;
   2) using a nucleic acid amplification instrument and/or a sequencing instrument with a primer comprising at least 15 consecutive bases of SEQ ID NO: 4 or SEQ ID NO: 5, with the proviso that the primer does not have the sequence of SEQ ID No. 6 or SEQ ID No. 7 to measure the number of anellovirus DNA sequences in the sample by detecting Torque teno virus (TTV) DNA, Torque teno midi virus (TTMDV) DNA, and Torque teno mini virus (TTMV) DNA in the sample to generate a combined value of the measured number of anellovirus; and 3) using a nucleic acid amplification instrument and/or a sequencing instrument to measure the number of total DNA sequences in the sample;

4) generating the value by determining a ratio of the measured number of anellovirus DNA sequences to the measured number of total DNA sequences in the sample, wherein if the value is higher than $0.2 \times 10^{-4}$ in the sample, the human subject is immunosuppressed.

15. The method of claim 14, wherein PCR is used to obtain the measured number of anellovirus DNA sequences using a pair of primers comprising at least 15 consecutive bases of SEQ ID NO: 4 or 5.

16. The method of claim 15, further comprising a labelled probe that hybridizes between the pair of primers.

17. The method of claim 1, wherein the sample is a blood sample.

18. The method of claim 14, wherein the sample is a blood sample.

* * * * *